(12) United States Patent
Bowsher

(10) Patent No.: US 8,646,449 B2
(45) Date of Patent: Feb. 11, 2014

(54) ANTI-ASPHYXIATION VALVES

(75) Inventor: Richard Francis Bowsher, Reading (GB)

(73) Assignee: Intersurgical AG, Vaduz (LI)

( * ) Notice: Subject to any disclaimer, the term of this patent is extended or adjusted under 35 U.S.C. 154(b) by 744 days.

(21) Appl. No.: 12/742,708

(22) PCT Filed: Nov. 13, 2008

(86) PCT No.: PCT/GB2008/051056
§ 371 (c)(1),
(2), (4) Date: May 13, 2010

(87) PCT Pub. No.: WO2009/063238
PCT Pub. Date: May 22, 2009

(65) Prior Publication Data
US 2010/0263669 A1    Oct. 21, 2010

(30) Foreign Application Priority Data

Nov. 13, 2007 (GB) .................................. 0722247.4

(51) Int. Cl.
*A61M 11/00* (2006.01)
(52) U.S. Cl.
USPC ................................ 128/205.24; 128/201.28
(58) Field of Classification Search
USPC ............. 128/201.28, 203.11, 204.19, 204.26, 128/204.27, 205.24, 206.15, 207.12, 205.25
See application file for complete search history.

(56) References Cited

U.S. PATENT DOCUMENTS

| | | | |
|---|---|---|---|
| 3,680,555 A | 8/1972 | Warncke | |
| 4,622,964 A | 11/1986 | Flynn | |
| 4,898,174 A | 2/1990 | Fangrow, Jr. | |
| 4,960,121 A | 10/1990 | Nelson et al. | |
| 4,989,596 A | 2/1991 | Macris et al. | |
| 5,086,768 A * | 2/1992 | Niemeyer | ................ 128/205.24 |
| 5,647,355 A | 7/1997 | Starr et al. | |

(Continued)

FOREIGN PATENT DOCUMENTS

| | | |
|---|---|---|
| DE | 29807489 U1 | 7/1998 |
| DE | 19818497 C1 | 2/2000 |

(Continued)

OTHER PUBLICATIONS

PCT International Search Report for corresponding PCT/GB2008/051056, dated Apr. 8, 2009.

(Continued)

*Primary Examiner* — Steven Douglas
(74) *Attorney, Agent, or Firm* — LeClairRyan, a Professional Corporation

(57) ABSTRACT

An anti-asphyxiation valve is disclosed, which is adapted for incorporation within a breathing circuit including a ventilator. The valve comprises one or more apertures for enabling passage of gas between the breathing circuit and the atmosphere, and a valve member deformable between an open configuration in which the one or more apertures are at least partially exposed and the passage of gas therethrough is enabled, and a closed configuration in which the valve member occludes the one or more apertures and the passage of gas therethrough is substantially prevented. The valve member is adapted such that the pressure within the breathing circuit at which the valve member deforms from the open configuration to the closed configuration is greater than the pressure within the breathing circuit at which the valve member deforms from the closed configuration to the open configuration.

16 Claims, 8 Drawing Sheets

(56) References Cited

U.S. PATENT DOCUMENTS

| | | | |
|---|---|---|---|
| 6,467,483 B1 | 10/2002 | Kopacko et al. | |
| 6,530,373 B1 | 3/2003 | Patron et al. | |
| 7,007,696 B2 | 3/2006 | Palkon et al. | |
| 2003/0019496 A1 | 1/2003 | Kopacko et al. | |
| 2004/0094157 A1* | 5/2004 | Dantanarayana et al. | 128/206.21 |
| 2004/0255948 A1 | 12/2004 | Smith et al. | |
| 2006/0076017 A1 | 4/2006 | Walker et al. | |
| 2006/0107960 A1 | 5/2006 | Smart | |
| 2009/0260628 A1* | 10/2009 | Flynn, Sr. | 128/203.28 |

FOREIGN PATENT DOCUMENTS

| | | |
|---|---|---|
| EP | 1258266 A1 | 5/2002 |
| EP | 1225945 B1 | 7/2002 |
| GB | 2176407 A | 12/1986 |
| GB | 2397244 A | 7/2004 |
| WO | 94/06514 A1 | 3/1994 |
| WO | 0132250 A1 | 5/2001 |
| WO | 2005094928 A1 | 10/2005 |
| WO | 2007/045008 A1 | 4/2007 |
| WO | 2007/143792 A1 | 12/2007 |

OTHER PUBLICATIONS

GB Intellectual Property Office Search Report for corresponding GB0820783.0, dated Feb. 17, 2009.

Search and Examination Report for corresponding application GB0820783.9 (dated Jun. 18, 2012).

* cited by examiner

ANTI-ASPHYXIATION VALVES

This application is a national stage application under 35 U.S.C. §371 from PCT Application No. PCT/GB2008/051056, filed Nov. 13, 2008, which claims the priority benefit of Great Britain Application No. 0722247.4, filed Nov. 13, 2007.

this invention relates to anti-asphyxiation valves and in particular to anti-asphyxiation valves for use in non-invasive ventilation.

Non-invasive ventilation is a process by which a flow of respiratory gas is delivered to the airway of a user through a non-invasive interface device, which is generally a respiratory mask, and hence without using an endotracheal or tracheostomy tube. Non-invasive ventilation is typically used to manage both chronic and acute respiratory failure, and also other medical disorders, such as sleep apnea.

Leakage from a respiratory mask during use is undesirable because it reduces alveolar ventilation and synchrony between the user and the ventilator, and hence respiratory masks for use in non-invasive ventilation are generally adapted to form an effective seal against the user's face. For this reason, an anti-asphyxiation valve is typically provided in the breathing circuit to enable the user to inhale and exhale air to and from the atmosphere, in the event that the ventilator fails.

Conventional anti-asphyxiation valves can be costly to manufacture, however, and hence relatively expensive to replace. In particular, the precise arrangement of the valve is typically critical in order for the valve to remain closed during normal use, but remain open during failure of the ventilator. Furthermore, conventional anti-asphyxiation valves are often separate components that need to be incorporated into the breathing circuit, and may be relatively bulky components.

There has now been devised an improved anti-asphyxiation valve, an improved non-invasive ventilation interface device and improved respiratory apparatus which overcome or substantially mitigate the above-mentioned and/or other disadvantages associated with the prior art.

According to a first aspect of the invention, there is provided an anti-asphyxiation valve adapted for incorporation within a breathing circuit including a ventilator, the valve comprising one or more apertures for enabling passage of gas between the breathing circuit and the atmosphere, and a valve member deformable between an open configuration in which the one or more apertures are at least partially exposed and the passage of gas therethrough is enabled, and a closed configuration in which the valve member occludes the one or more apertures and the passage of gas therethrough is substantially prevented, wherein the valve member is adapted such that the pressure within the breathing circuit at which the valve member deforms from the open configuration to the closed configuration is greater than the pressure within the breathing circuit at which the valve member deforms from the closed configuration to the open configuration.

The anti-asphyxiation valve according to the invention is particularly advantageous when incorporated into an interface device for use in non-invasive ventilation, such as a respiratory mask. Hence, according to a further aspect of the invention, there is provided a non-invasive ventilation interface device including an anti-asphyxiation valve as described above. The non-invasive ventilation interface device is typically a respiratory mask.

By "pressure within the breathing circuit" is meant the pressure of the gas within the part of the breathing circuit into which the anti-asphyxiation valve is incorporated. Hence, where the anti-asphyxiation valve is incorporated into a non-invasive ventilation interface device, this "pressure within the breathing circuit" is the pressure within the interface device.

The anti-asphyxiation valve and the non-invasive ventilation interface device according to these aspects of the invention are advantageous principally because the valve may be readily adapted such that (i) during normal operation of the ventilator the valve member reliably remains in its closed configuration, (ii) on failure of the ventilator the valve member is deformed into its open configuration, and (iii) the valve member reliably remains in its open configuration during unaided breathing of the user from the atmosphere.

The anti-asphyxiation valve according to the invention is preferably an integral part of the interface device. In particular, the one or more apertures of the anti-asphyxiation valve are preferably formed in a wall of the interface device, and the valve member is preferably mounted to an interior surface of the interface device. Hence, according to a further aspect of the invention, there is provided a non-invasive ventilation interface device comprising an anti-asphyxiation valve as described above, in which the one or more apertures of the anti-asphyxiation valve are formed in a wall of the interface device, and the valve member is mounted to an interior surface of the interface device. The non-invasive ventilation interface device is typically a respiratory mask.

The interface device according to this aspect of the invention is advantageous principally because although an anti-asphyxiation valve is incorporated into the interface device, the interface device may have a simple construction that is inexpensive to manufacture. Furthermore, the anti-asphyxiation valve may be entirely separate from one or more ports of the interface device through which gases flow into, and out of, the interface device from the remainder of the breathing circuit, and hence the effect on the valve of normal variations in airflow within the breathing circuit may be reduced.

The valve member is preferably resiliently biased into its open configuration. In particular, deformation of the valve member away from the open configuration preferably causes internal stresses within the valve member that act to reform the valve member back to its open configuration. These internal stresses are typically compression or tensile stress. Most preferably, the valve member is formed of an elastomeric material, such as silicone, which is manufactured in its open configuration, for example by injection or compression moulding.

The force resiliently biasing the valve member into its open configuration preferably increases as the deformation away from the open configuration increases. However, in order for the valve member to be adapted such that the closing pressure is greater than the opening pressure, as discussed above, the valve member is preferably resiliently biased into its open configuration by a force that peaks in a configuration of the valve member that is intermediate of the open and closed configurations, such that the biasing force in the closed configuration is less than the peak biasing force between the open and closed configurations.

The peak biasing force of the valve member, into the open configuration, determines the pressure within the breathing circuit at which the valve member deforms from the open configuration to the closed configuration. This closing pressure is preferably substantially equal to, or greater than, the Positive End Expiratory Pressure (PEEP) applied to the breathing circuit. Furthermore, the valve member is preferably adapted such that the anti-asphyxiation valve remains open during unaided breathing of the user, when the ventilator is not functioning.

Where the valve member is biased into its open configuration at all points between the open and closed configurations, the pressure within the breathing circuit at which the valve member deforms from the closed configuration to the open configuration will be greater than atmospheric pressure. Most preferably, this opening pressure is less than the Positive End Expiratory Pressure (PEEP) applied to the breathing circuit, so that the anti-asphyxiation valve remains closed during normal operation of the breathing circuit and ventilator.

In alternative embodiments, the valve member may be resiliently biased into its open configuration until the valve member attains its closed configuration, wherein the stresses within the valve member are substantially at equilibrium, such that the pressure within the breathing circuit at which the valve member deforms from the closed configuration to the open configuration will be substantially equal to atmospheric pressure.

In further alternative embodiments, the valve member may be resiliently biased into its open configuration during deformation until the valve member reaches a transitional configuration, beyond which the valve member becomes resiliently biased into its closed configuration. In these embodiments, the pressure within the breathing circuit at which the valve member deforms from the closed configuration to the open configuration will be less than atmospheric pressure. The anti-asphyxiation valve will therefore remain closed until the pressure within the breathing circuit is reduced below atmospheric pressure by inhalation of the user. In addition, this resilient biasing of the valve member into its closed configuration will improve the seal between the valve member and the associated valve seat in the closed configuration.

The valve member is preferably adapted such that deformation of the valve member between the open and closed configurations causes at least part of the valve member to become stressed under either compression or tension, and this stress causes the resilient biasing of the valve member discussed above. In order that the valve member is resiliently biased into its open configuration by a force that peaks between the open and closed configurations, as discussed above, the valve member preferably has a configuration including an arcuate or folded member that is straightened on deformation away from its open configuration, and may be at least partially inverted in its closed configuration.

In presently preferred embodiments, the valve member comprises a continuous wall having a substantially conical or pyramidal configuration, and the valve member is preferably mounted at the tip of the conical or pyramidal wall to an interior surface of the interface device. This is a particularly convenient arrangement in that although an anti-asphyxiation valve is incorporated into non-invasive ventilation interface device, such as a respiratory mask, the interface device may have a simple construction that is inexpensive to manufacture.

Hence, according to a further aspect of the invention, there is provided a non-invasive ventilation interface device comprising an anti-asphyxiation valve including one or more apertures for enabling passage of gas between the breathing circuit and the atmosphere, and a valve member deformable between an open configuration in which the one or more apertures are at least partially exposed and the passage of gas therethrough is enabled, and a closed configuration in which the valve member occludes the one or more apertures and the passage of gas therethrough is substantially prevented, wherein the one or more apertures of the anti-asphyxiation valve are formed in a wall of the interface device, and the valve member has a continuous wall having a substantially conical or pyramidal configuration, which is mounted at the tip of the conical or pyramidal wall to an interior surface of the interface device. The non-invasive ventilation interface device is typically a respiratory mask.

The valve member preferably comprises an opening at the tip of the conical or pyramidal wall, and an open base. Where the valve member has a substantially pyramidal configuration, the valve member may have any one of a variety of polygonal cross-sectional shapes, eg square, hexagonal, octagonal. However, the valve member preferably has a substantially conical configuration, and preferably has a substantially circular cross-sectional shape.

The anti-asphyxiation valve preferably includes a valve seat that surrounds the one or more apertures, and preferably also surrounds each individual aperture. Where the anti-asphyxiation valve is incorporated into an interface device, the valve seat is preferably defined by part of the interior surface of the interface device, which is preferably raised relative to the surrounding interior surface.

The valve member is preferably mounted to an interior surface of the interface device, such that deformation of the valve member into its closed configuration causes the valve member to engage the valve seat. The form of the valve seat preferably therefore determines the closed configuration of the valve member. In particular, where the valve member is substantially conical or pyramidal in shape, the valve member is preferably adapted to be flattened on deformation away from its open configuration, and may have either (i) a closed configuration in which the inclination of the wall of the valve member is reduced relative to the open configuration, (ii) a closed configuration in which the wall of the valve member is substantially flat, or (iii) a closed configuration in which the valve member is at least partially inverted relative to the open configuration.

Furthermore, the form of the valve seat, and hence the closed configuration of the valve member, preferably at least partially determines the pressure within the interface device at which the valve member deforms from the closed configuration to the open configuration. For instance, where the valve member has a closed configuration in which the inclination of the wall of the valve member is reduced relative to the open configuration, the pressure within the interface device at which the valve member deforms from the closed configuration to the open configuration will be greater than atmospheric pressure, as discussed in more detail above. Where the valve member has a closed configuration in which the wall of the valve member is substantially flat, the pressure within the interface device at which the valve member deforms from the closed configuration to the open configuration will be substantially equal to atmospheric pressure. Where the valve member has a closed configuration in which the valve member is at least partially inverted relative to the open configuration, the pressure within the interface device at which the valve member deforms from the closed configuration to the open configuration will be less than atmospheric pressure, as discussed in more detail above.

The substantially conical or pyramidal valve member is preferably mounted relative to the one or more apertures by a retainer that extends through an opening at the tip of the valve member. The valve member is preferably not bonded to the retainer, such that deformation of the valve member will not cause stresses at the interface between the valve member and the retainer. In particular, the retainer preferably includes an enlarged head having a greater width than the width of the valve member opening, such that the valve member engages the retainer with a snap fit.

Where the valve member is able to be inverted, such as in the case of a conical or pyramidal valve member, the valve member preferably includes an indication regarding the correct configuration for assembly of the valve. In particular, such an indication may take the form of a formation, such as a rib, on one of the surfaces of the valve member.

The interface device preferably includes a port for connection of the interface device to the breathing circuit. The connection port is preferably therefore adapted to enable inhalation gases to be supplied to the interface device, and exhalation gases to be removed from the interface device, during normal use. The anti-asphyxiation valve and the connection port are preferably entirely separate parts of the interface device, and are preferably formed in distinct parts of the wall of the interface device. The interface device preferably also includes a flow deflector interposed between the connection port and the anti-asphyxiation valve. The flow deflector is preferably adapted to shield the anti-asphyxiation valve from the connection port, thereby reducing the proportion of gas that flows directly between the connection port and the anti-asphyxiation valve when the valve member is in its open configuration.

The interface device preferably also includes one or more vent openings in the wall of the interface device, which have an area that is substantially less than the area of the one or more apertures of the anti-asphyxiation valve. These vent openings preferably facilitate removal of exhalation gases, and in particular carbon dioxide, from the interface device during normal use. The interface device may also include an additional port, which enables a supplementary supply of oxygen to be connected to the interface device and supplied to the user, for example.

The interface device is typically a respiratory mask, which preferably comprises a mask body, and one or more sealing components extending from the peripheral edge of the mask body and defining a contact surface that contacts the face of the user during use. The respiratory mask preferably defines a cavity that accommodates the user's nose and mouth when fitted to the user. The contact surface of the one or more sealing components preferably extends along the entire peripheral edge of the mask body so as to seal the cavity against the face of a user during use. Each sealing component preferably comprises one or more sealing members that define the contact surface. Each sealing member is preferably formed of a material that deforms into conformity with the contours of a user's face during use. In particular, each sealing member is preferably formed of an elastomeric material.

The mask body is preferably formed as a single component of a relatively rigid material. In particular, the mask body is preferably formed so that it maintains its shape when subjected to normal handling, packaging and storage conditions. The mask body is preferably formed from plastics material in an injection moulding process. Most preferably, the mask body is formed of polypropylene.

The one or more sealing components are preferably formed from an elastomeric material, which is most preferably a Styrene-Ethylene-Butylene-Styrene (SEBS)-based thermoplastic elastomer, or silicone. The mask body and the one or more sealing components may be bonded together. However, in presently preferred embodiments, the mask body includes one or more formations adapted to engage corresponding formations of the one or more sealing components, in order that the mask body and the one or more sealing components are releasably engageable with each other, with a snap fit.

As discussed above, the mask body preferably includes one or more retaining formations that act to retain the valve member during use. The one or more retaining formations are preferably formed integrally with the mask body, such that the mask body including the one or more retaining formations is defined by a single component. In particularly preferred embodiments, the mask body including the one or more retaining formations is formed as a single component from plastics material in an injection moulding process.

According to a further aspect of the invention, there is provided respiratory apparatus comprising a ventilator and a non-invasive ventilation interface device according to the invention.

A preferred embodiment of the invention will now be described in greater detail, by way of illustration only, with reference to the accompanying drawings, in which FIG. 1 is a perspective view of a respiratory mask according to the invention;

Figure 1:
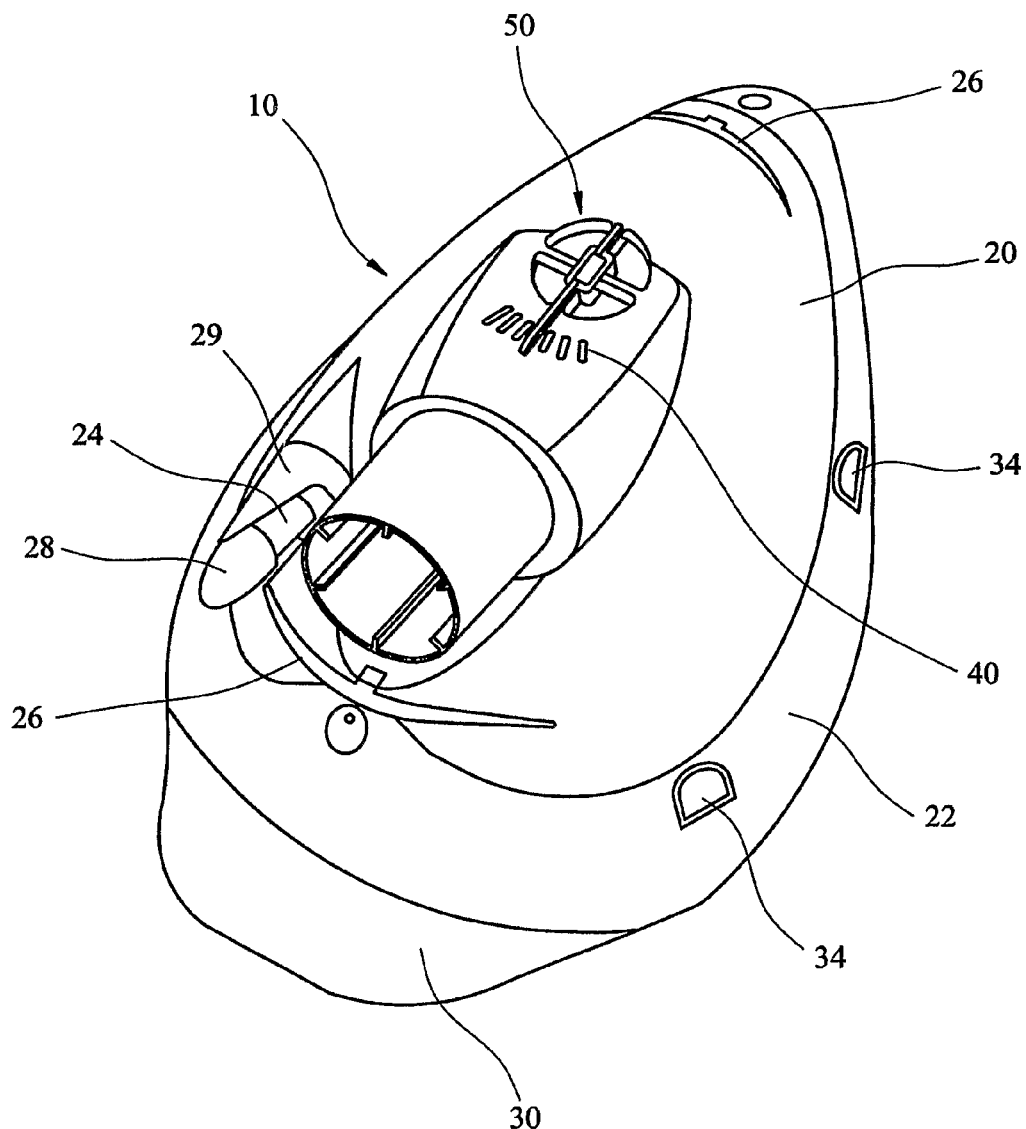
Figure 2:
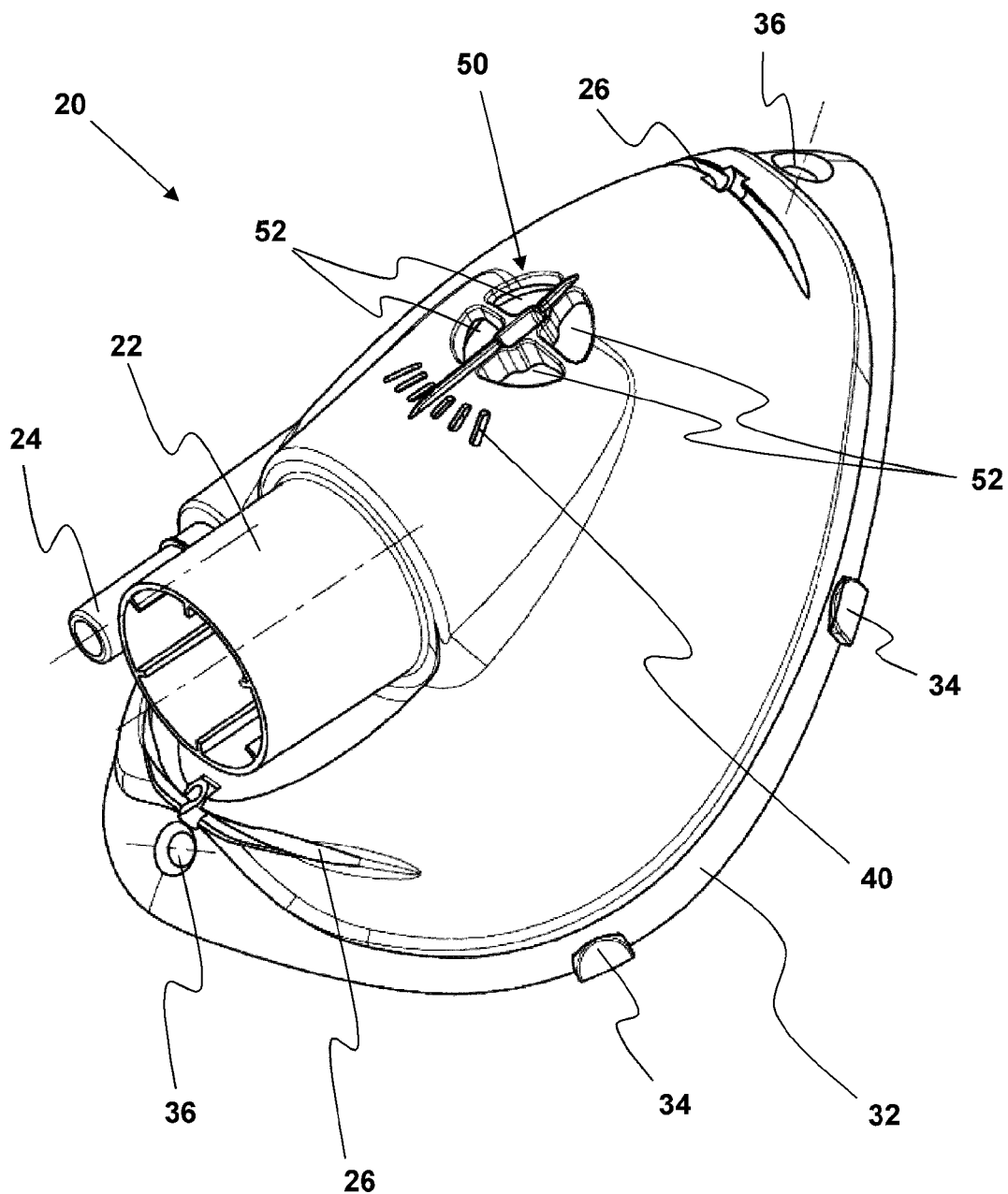
FIG. 2 is a first perspective view of a mask body, which forms part of the respiratory mask of FIG. 1.
Figure 3:
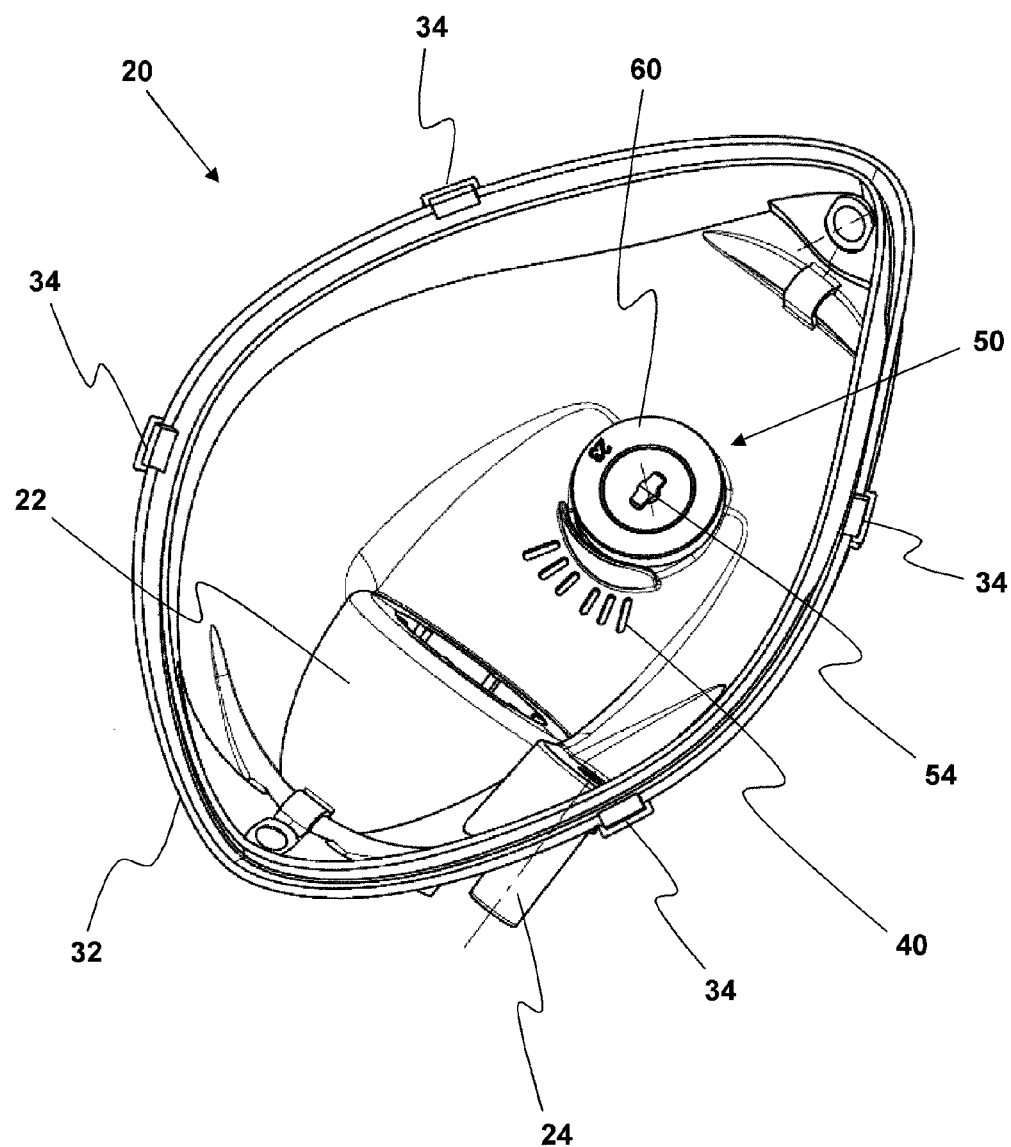
FIG. 3 is a second perspective view of the mask body.

FIG. 1 shows a respiratory mask according to the invention, which is generally designated 10. The respiratory mask 10 comprises a mask body 20 and a sealing component 30, which are releasably fastened together. The mask body 20 is injection moulded in a relatively rigid plastic material, such as polypropylene, and the sealing component 30 is injection moulded in a more compliant material, such as a thermoplastic elastomeric material. FIGS. 2 and 3 show the mask body 20 in isolation from the sealing component 30.

The mask body 20 is dimensioned and configured to define a cavity that accommodates the nose and mouth of a user, during use, whilst the sealing component 30 seals the mask body 20 against the face of the user. The mask body 20 also includes a conventional, tubular connection port 22 for connection of the mask body 20 to a ventilator, and an additional port 24 for connection of the mask body 20 to ancillary apparatus, such as a supplementary supply of oxygen or $CO_2$ measurement apparatus, if necessary. A cap 28 and a guard 29, which are formed of a similar material to the sealing component 30, are also provided, as shown in FIG. 1. The cap 28 acts to seal the additional port 24 when not in use, and the guard 29 protects the connection between the additional port 24 and a connected tube, such as an oxygen supply tube, during use.

A groove 26 is provided at each end of the exterior surface of the mask body 20. The grooves 26 are adapted to fasten the mask body 20 to suitable headgear (not shown in the Figures), such as that described in a co-pending UK patent application in the name of the applicant. Each groove 26 is orientated transversely relative to the longitudinal axis of the mask 10, and has an entrance opening of slightly reduced width so that an engagement thread of the headgear is received with a snap fit.

The mask body 20 also includes a peripheral flange 32, which has two projections 34 on each side of the mask body 20 and a recess 36 at each end of the mask body 20. These projections 34 and recesses 36 are each adapted to engage a corresponding formation of the sealing component 30, with a snap fit, thereby fastening the mask body 20 and the sealing component 30 together.

The mask body 20 also includes a series of six vent openings 40 in a wall of the mask body 20, and an anti-asphyxiation valve 50 adjacent to the vent openings 40. The vent openings 40 are adapted to enable carbon dioxide not returned to the breathing circuit through the connection port 22, during use, to escape into the atmosphere. The anti-asphyxiation valve 50 is constructed in a wall of the mask body 20, such that the valve 50 is entirely separate from the connection port 22.

Figure 6:
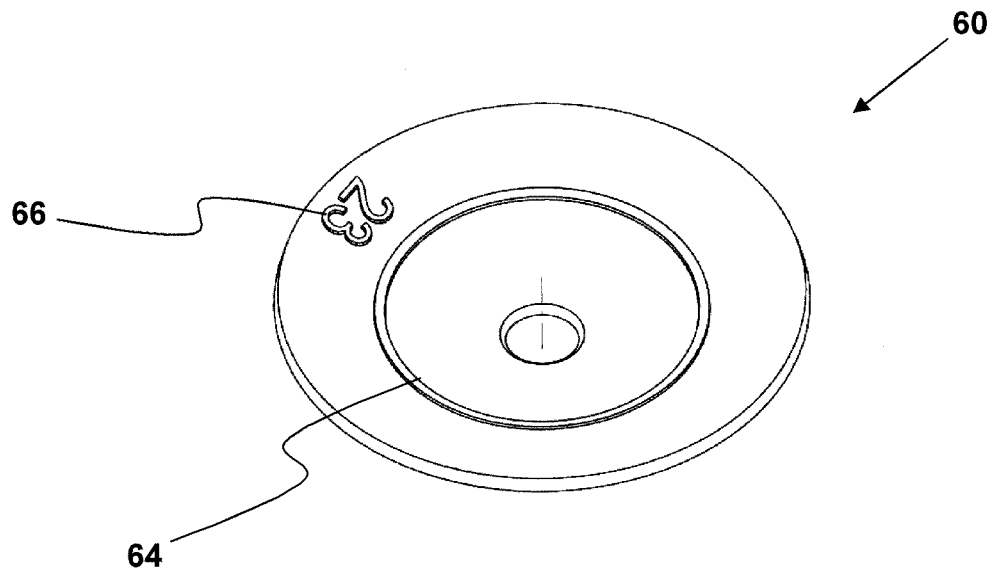
FIG. 6 is a perspective view of a valve member, which forms part of the respiratory mask of FIG. 1.
Figure 7:
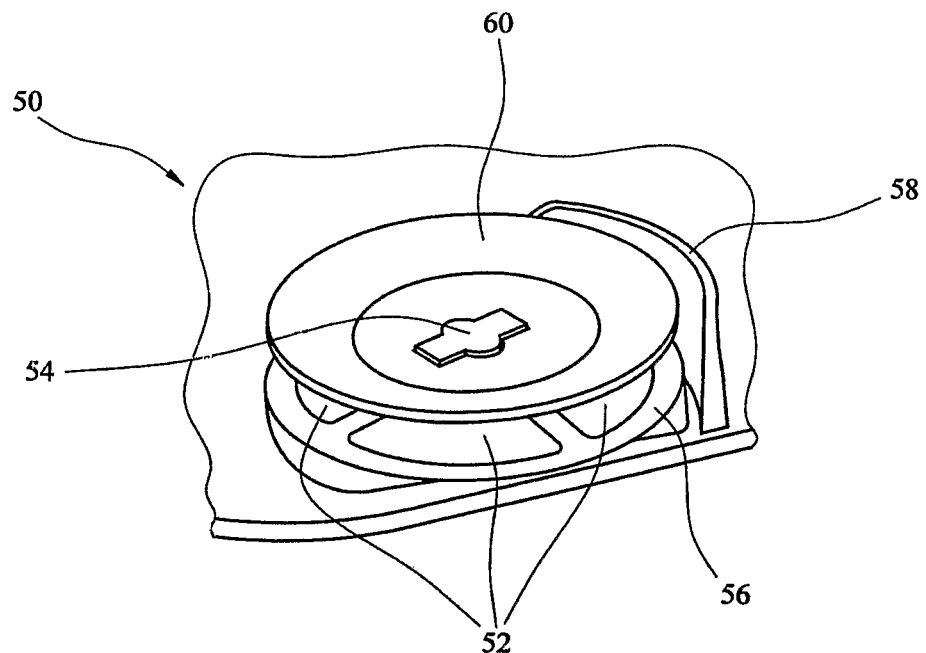
FIG. 7 is a perspective view of an anti-asphyxiation valve according to the invention, which forms part of the respiratory mask of FIG. 1.

The anti-asphyxiation valve 50 comprises four distinct openings 52 in a wall of the mask body 20, which are arranged in a circular configuration in which the openings are separated by a cross-shaped separator member. A deformable valve member 60 is provided, which is injection moulded in a thermoplastic elastomeric material. The valve member 60 is adapted to occlude and hence seal the openings 52 in a closed configuration. In particular, the valve member 60 is generally conical in shape, with a central circular opening, as shown most clearly in FIG. 6. The valve member 60 also includes a clearly visible annular rib 64 on one of its major surfaces, in order to indicate the correct configuration of the valve member 60, and also raised indicia 66 that indicate the cavity in which the valve member 60 was manufactured.

The valve member 60 is mounted to an interior surface of the mask body 20 by a retainer 54 that projects from the centre of the cross-shaped separator member between the openings 52. The retainer 54 comprises a cylindrical body with an enlarged head, such that the retainer 54 engages the central opening of the valve member 60 with a snap fit. In particular, the valve member 60 is not bonded to the retainer 54, but is retained by means of the enlarged head of the retainer 54 having a greater width than the diameter of the opening in the valve member 60.

Figure 4:
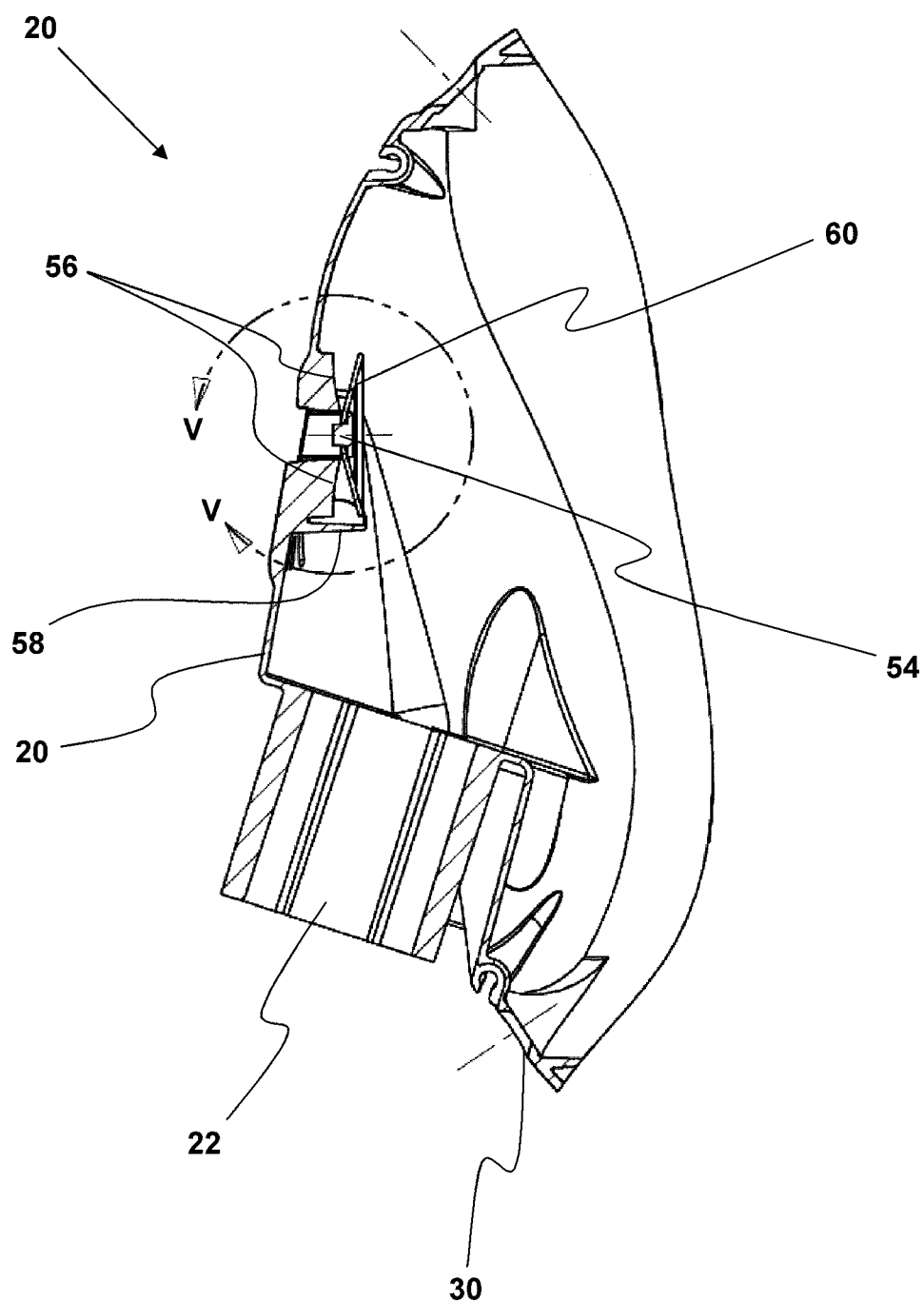
FIG. 4 is a cross-sectional view of the respiratory mask of FIG. 1.
Figure 5:
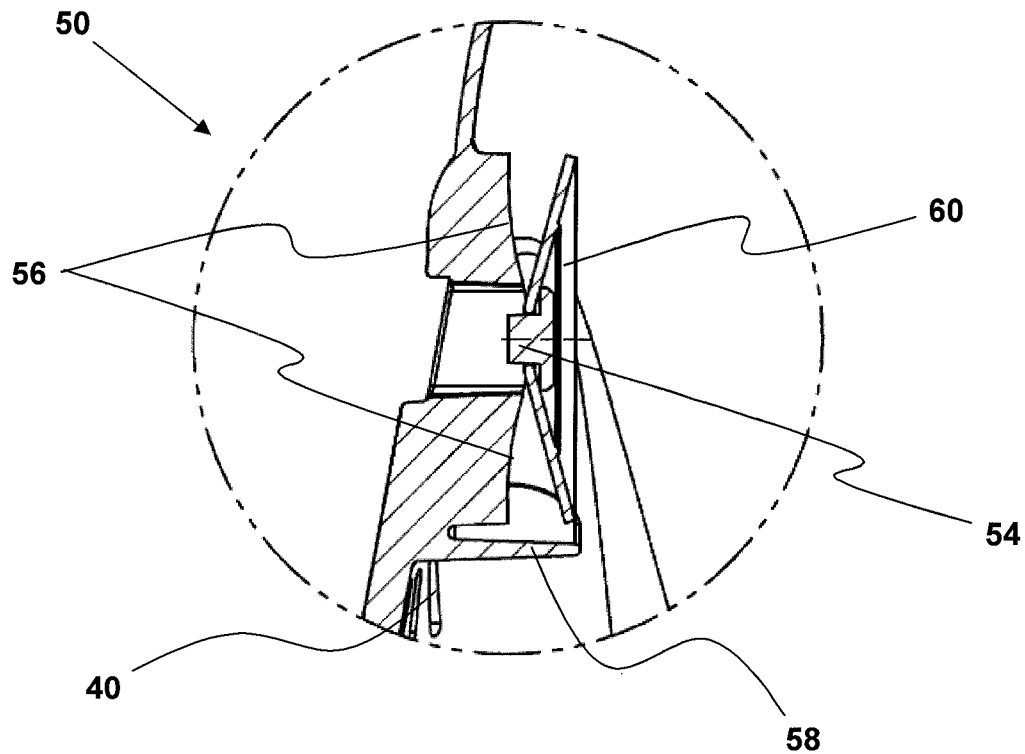
FIG. 5 is a cross-sectional view of the part of the respiratory mask encompassed by the line V-V in FIG. 3.

The interior surface of the mask body 20 surrounding the four openings 52, including the interior surface of the cross-shaped separator member, is raised relative to the surrounding interior surface of the mask body 20, and defines a valve seat 56 suitable for engagement by the valve member 60 in the closed configuration. As shown most clearly in FIGS. 4 and 5, the valve seat 56 gradually reduces in height towards its outer edge, relative to the retainer 54 and the centre of the valve member 60, and is also slightly concave in form, such that the valve seat 56 is inclined in an opposite direction to the inclination of the valve member 60 in its open configuration. The valve member 60 may therefore be deformed into an at least partially inverted configuration in which the valve member lies alongside, and hence engages, the valve seat 56.

In the open configuration of the valve 50, which is shown in FIGS. 4, 5, 7 and 8 (position A), the valve member 60 is arranged in its inherent conical configuration, such that the valve member 60 is separated from the openings 52 and the associated valve seat 56. In this configuration, gases are able to flow between the mouth of the user and the atmosphere, via the openings 52 of the valve 50. The user is therefore able to breathe atmospheric air when the valve 50 is in its open configuration. The valve 50 also includes a flow deflector 58, which is disposed between the valve 50 and the vent openings 40, on the side of the valve 50 that faces the connection port 22. The flow deflector 58 is adapted to shield the valve 50 from the connection port 22, thereby reducing the proportion of gas that flows directly between the connection port 22 and the valve 50 in the open configuration.

When the pressure differential between the interior of the mask body 20 and atmospheric pressure exceeds a particular threshold, the valve member 60 will be deformed towards the valve seat 56 of the valve 50. In particular, the angle of inclination of the wall of the valve member 60 will reduce. In these transitional configurations, the valve member 60 will be in tension, and these internal stresses will resiliently bias the valve member 60 towards the open configuration. However, further deformation of the valve member 60 caused by the pressure differential will result in the wall of the valve member 60 becoming substantially flat, and then inclined in the opposite direction to its inclination in the open configuration. Beyond a particular threshold, the internal stresses of the valve member 60 will cause it to become resiliently biased into an inverted configuration, and hence into engagement with the valve seat 56 and its closed configuration, as indicated by position B in FIG. 8. In this configuration, the valve member 60 seals the openings 52 of the valve 50 so that airflow between the mask body 20 and the atmosphere, through the valve 50, is prevented.

Figure 8:
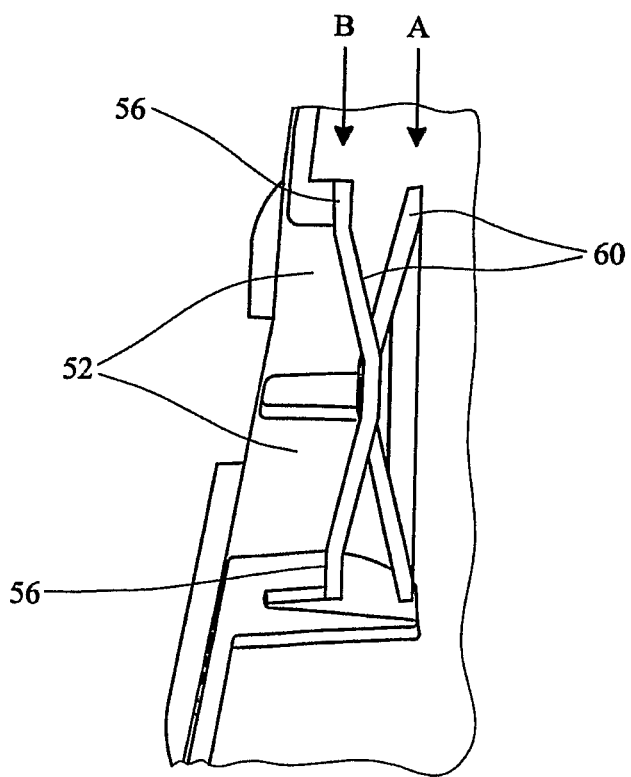
FIG. 8 is a schematic cross-sectional view of the anti-asphyxiation valve, which illustrates open and closed configurations of the valve.

In use, the respiratory mask 10 is fitted to a user with the valve 50 in its open configuration, as indicated by position A in FIG. 8. The respiratory mask 10 is arranged with the nose and mouth of the user within the cavity defined by the mask body 20, and the sealing component 30 contacting a surrounding area of the user's face. Headgear (not shown in the Figures) attached to the respiratory mask 10 urges the sealing component 30 against the user's face in order that an effective seal is provided about the periphery of the respiratory mask 10. Finally, the connection port 22 is connected to a breathing circuit including a ventilator (not shown in the Figures).

Until the ventilator is initiated, and hence until gas is supplied to the mask 10, the user is able to breathe air from the atmosphere through the anti-asphyxiation valve 50. The valve 50 is therefore adapted to close at a pressure differential, and an airflow into the mask 10, that is greater than that induced by normal, unaided breathing of the user wearing the mask 10.

Figure 9:
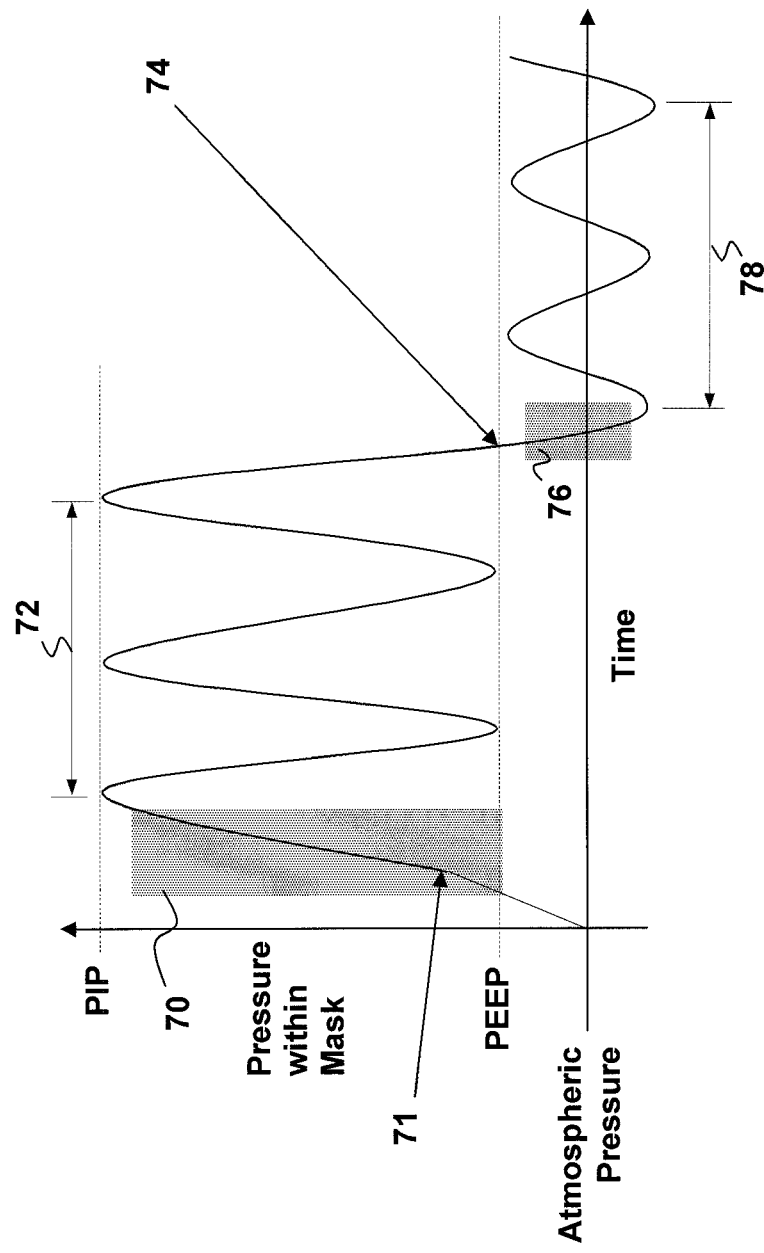
FIG. 9 illustrates an example of the pressure within the mask in different operational circumstances, during use.
Figure 10:
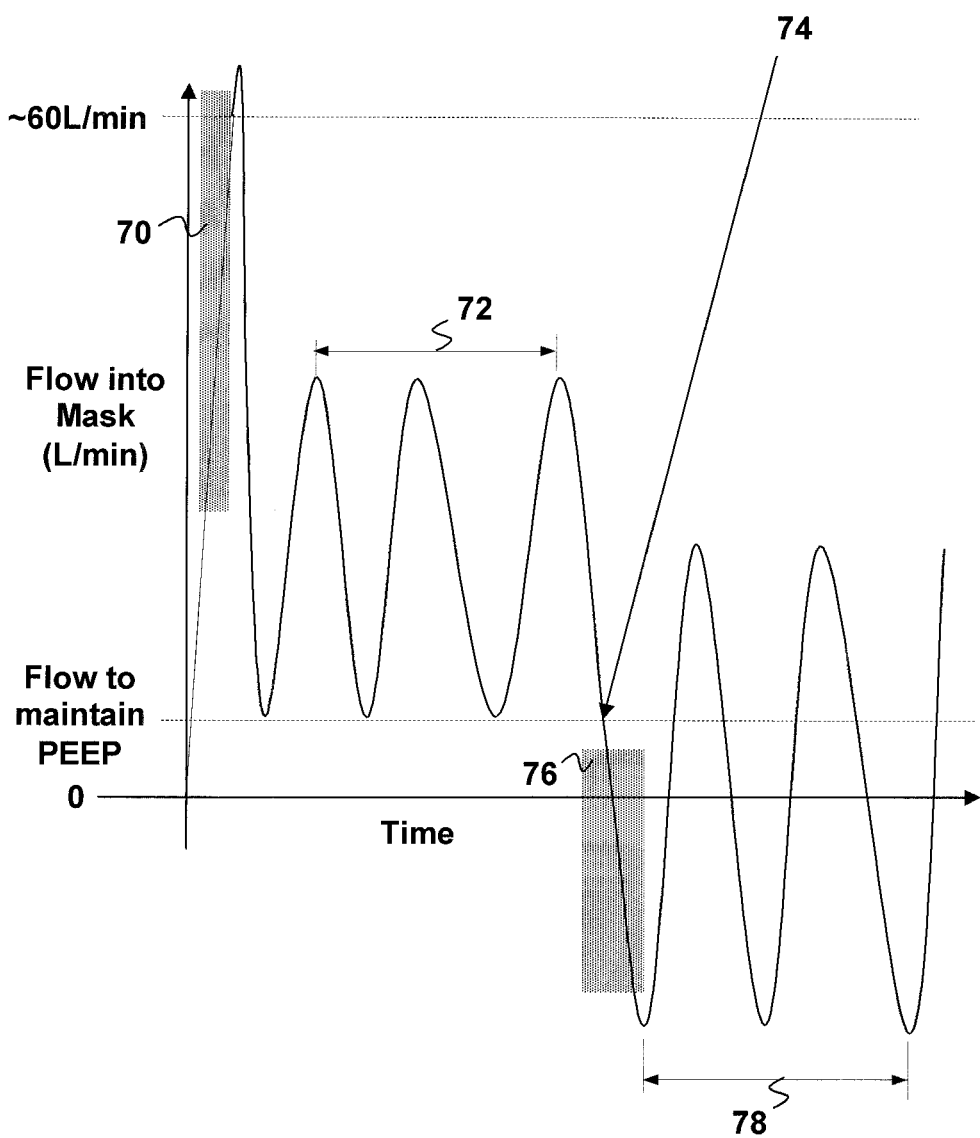
FIG. 10 illustrates an example of the rate of flow of gas into the mask in different operational circumstances, during use.

An example of the variation of the pressure within the respiratory mask 10 and the airflow into the mask 10 is shown in FIGS. 9 and 10, respectively, including initiation of the ventilator and associated breathing circuit, normal ventilator operation (range 72), and unaided breathing through the anti-asphyxiation valve (range 78) following failure of the ventilator (at point 74).

Upon initiation of the ventilator, the airflow into the mask 10 through the connection port 22 will gradually increase beyond the airflow required to maintain a typical Positive End Expiratory Pressure (PEEP), such as approximately 2.0 cmH$_2$O (200 Pa), during use. This airflow causes the pressure within the mask 10 to increase, as shown by FIGS. 9 and 10, until the pressure within the mask 10 is sufficient to cause the valve member 60 to be deformed from its open configuration into engagement with the valve seat 56 and hence its closed configuration, as indicated by position B in FIG. 8. The valve 50 is adapted so that the airflow into the mask 10 required to close the valve 50 is greater than the airflow generated by a user during unaided breathing, and the pressure with the mask 10 required to close the valve 50 is greater than the PEEP of the breathing circuit. This closure of the valve 50 may therefore occur at a point within area 70 in FIGS. 9 and 10, for example, or indeed at a greater flow or pressure. However, in this embodiment, the airflow required to close the valve 50 is approximately 60 L/min (1.0 Ls$^{-1}$), and closure of the valve 50 occurs at point 71 in FIG. 9.

Once the valve 50 is closed, the user is able to breathe within the breathing circuit. The pressure within the mask 10 will vary during the user's breathing cycle between approximately the PEEP of the breathing circuit, to a Peak Inspiratory Pressure (PIP), which is typically of the order of 5-50 cmH$_2$O (0.5–5 kPa). During normal operation of the ventilator, the pressure within the mask and the airflow into the mask will vary as illustrated by range 72 of FIGS. 9 and 10.

In the event that the ventilator fails, and hence airflow into the mask 10 from the breathing circuit ceases, subsequent inhalation by the user, and hence airflow out of the mask 10, will cause the pressure within the mask body 20 to fall below the PEEP of the breathing circuit, and typically to a pressure that is lower than atmospheric pressure. When the pressure within the mask 10 is sufficiently reduced, the pressure differential between the interior of the mask 10 and atmospheric pressure will cause the valve member 60 to be deformed from its closed configuration into its open configuration, such that the valve member 60 is removed from the valve seat 56 and the openings 52 are exposed, as indicated by position A in FIG. 8. In FIGS. 9 and 10, failure of the ventilator occurs at point 74, and the valve 50 may be adapted to open at a point within area 76, for example. In the specific embodiment described above, the valve 50 will open when the pressure within the mask is at a threshold pressure that is less than atmospheric pressure. However, in other embodiments, the valve 50 may open when the pressure within the mask is at a threshold pressure that is equal to, or greater than, atmospheric pressure. In any case, however, the valve 50 will open when the pressure within the mask 10 is at a threshold pressure that is less than the PEEP of the breathing circuit, otherwise the valve 50 would open during normal ventilator operation.

In the open configuration of the valve 50, the user is able to breathe air from the atmosphere through the anti-asphyxiation valve 50. Since the airflow into the mask 10 required to close the valve 50 is greater than the airflow generated by a user during unaided breathing, the valve 50 will remain open until the ventilator becomes operational again.

The invention claimed is:

1. A non-invasive ventilation interface device comprising:
   an anti-asphyxiation valve comprising:
   one or more apertures for enabling passage of a gas between a breathing circuit and an atmosphere; and
   a valve member deformable between an open configuration in which the one or more apertures are at least partially exposed and the passage of the gas therethrough is enabled, and a closed configuration in which the valve member occludes the one or more apertures and the passage of the gas therethrough is substantially prevented; and
   wherein the one or more apertures of the anti-asphyxiation valve are formed in a wall of the interface device, and the valve member has a continuous wall having a substantially conical or pyramidal configuration, which is mounted at a tip of the conical or pyramidal wall to an interior surface of the interface device.

2. The non-invasive ventilation interface device as claimed in claim 1, wherein the interface device is a respiratory mask.

3. The non-invasive ventilation interface device as claimed in claim 1, wherein the valve member comprises an opening at a tip of the substantially conical or pyramidal wall, and an open base.

4. The non-invasive ventilation interface device as claimed in claim 1, wherein the anti-asphyxiation valve includes a valve seat that surrounds the one or more apertures.

5. The non-invasive ventilation interface device as claimed in claim 4, wherein the valve seat is defined by a part of the interior surface of the interface device.

6. The non-invasive ventilation interface device as claimed in claim 4, wherein the valve member is mounted to the interior surface of the interface device, such that deformation of the valve member into the closed configuration causes the valve member to engage the valve seat.

7. The non-invasive ventilation interface device as claimed in claim 1, wherein the valve member is mounted relative to the one or more apertures by a retainer that extends through an opening at the tip of the valve member.

8. The non-invasive ventilation interface device as claimed in claim 7, wherein the valve member is not bonded to the retainer.

9. The non-invasive ventilation interface device as claimed in claim 8, wherein the retainer comprises an enlarged head having a greater width than a width of the valve member opening, such that the valve member engages the retainer with a snap fit.

10. The non-invasive ventilation interface device as claimed in claim 1, wherein the valve member is adapted to be inverted, and the valve member further comprises an indication regarding a correct configuration for assembly of the anti-asphyxiation valve.

11. The non-invasive ventilation interface device as claimed in claim 1 further comprising a connection port for connection of the interface device to the breathing circuit, wherein the anti-asphyxiation valve and the connection port are entirely separate parts of the interface device, which are formed in distinct parts of the wall of the interface device.

12. The non-invasive ventilation interface device as claimed in claim 11, further comprising a flow deflector interposed between the connection port and the anti-asphyxiation valve.

13. The non-invasive ventilation interface device as claimed in claim 12, wherein the flow deflector is adapted to shield the anti-asphyxiation valve from the connection port, thereby reducing a proportion of gas that flows directly between the connection port and the anti-asphyxiation valve when the valve member is in the open configuration.

14. The non-invasive ventilation interface device as claimed in claim 1 further comprising one or more vent openings in the wall of the interface device, which have an area that is substantially less than an area of the one or more apertures of the anti-asphyxiation valve.

15. A respiratory apparatus comprising a ventilator and a non-invasive ventilation interface device as claimed in claim 1.

16. The non-invasive ventilation interface device as claimed in claim 1, wherein the valve member is adapted such that the pressure differential between the breathing circuit and atmospheric pressure at which the valve member deforms from the open configuration to the closed configuration is greater than the pressure differential between the breathing circuit and atmospheric pressure at which the valve member deforms from the closed configuration to the open configuration.

* * * * *